United States Patent [19]

Evers

[11] 4,108,884

[45] Aug. 22, 1978

[54] HYBRID PERFLUOROALKYLENE ETHER THIOIMIDATE ESTER MONOMERS

[75] Inventor: Robert C. Evers, Dayton, Ohio

[73] Assignee: The United States of America as represented by the Secretary of the Air Force, Washington, D.C.

[21] Appl. No.: 817,657

[22] Filed: Jul. 21, 1977

[51] Int. Cl.$^2$ ............................................. C07C 119/18
[52] U.S. Cl. ......................... 260/453 RW; 260/544 F; 260/465.6; 528/373
[58] Field of Search ................................ 260/453 RW

[56] References Cited

U.S. PATENT DOCUMENTS 3,523,132  11/1977  Dorfman et al. ............ 260/453 RW

OTHER PUBLICATIONS

Migrdichian, V., The Chemistry of Organic Cyanogen Compounds, Reinhold Publishing Corporation, 1947, p. 94

*Primary Examiner*—Lewis Gotts
*Assistant Examiner*—Robert C. Whittenbaugh
*Attorney, Agent, or Firm*—Joseph E. Rusz; Cedric H. Kuhn

[57] ABSTRACT

Perfluoroalkylene ether thioimidate esters derived primarily from tetrafluoroethylene oxide but end-capped with hexafluoropropylene oxide in the terminal positions of the perfluoroalkylene ether chain. The compounds are particularly useful as monomers to synthesize novel thermooxidatively and hydrolytically stable perfluoroalkylene ether bibenzozazole polymers having improved low temperature viscoelastic properties.

5 Claims, No Drawings

HYBRID PERFLUOROALKYLENE ETHER THIOIMIDATE ESTER MONOMERS

RIGHTS OF THE GOVERNMENT

The invention described herein may be manufactured and used by or for the Government of the United States for all governmental purposes without the payment of any royalty.

FIELD OF THE INVENTION

This invention relates to hybrid perfluoroalkylene ether thioimidate esters. In one aspect it relates to a process for preparing the esters.

BACKGROUND OF THE INVENTION

A large amount of research work has been carried out for the purpose of providing elastomeric polymers for various aerospace seal and sealant applications. For a polymer to fulfill completely the rigid requirements of such applications, it must be thermooxidatively and hydrolytically stable while also being capable of retaining its elastomeric properties at sub-zero temperatures. In the past it has been possible to synthesize polymers possessing two of these properties which are outstanding while one of the properties is less satisfactory than desired. Thus, in U.S. Pat. Nos. 3,846,376 and 3,994,861 polymers are disclosed by me that possess a broad use temperature range. However, the polymers are often hydrolytically unstable when exposed to humid conditions at elevated temperatures for extended periods of time. In my copending U.S. application Ser. No. 710,088, filed on July 30, 1976, and now issued as U.S. Pat. No. 4,064,109, polymers are disclosed that advance the art in meeting all three of the aforementioned requirements. Thus, the polymers are thermally and hydrolytically stable and have a fairly low glass transition temperature (Tg). Since the Tg of a polymer is an indication of the temperature at which it retains its viscoelastic properties, there is still a need for thermally and hydrolytically stable polymers having even lower glass transition temperatures.

It is a principal object of this invention, therefore, to provide compounds that can be used as monomers in synthesizing thermooxidatively and hydrolytically stable polymers having improved low temperature viscoelastic properties.

Another object of the invention is to provide a process for preparing hybrid perfluoroalkylene ether thioimidate ester monomers.

Other objects and advantages of the invention will become apparent to those skilled in the art upon consideration of the accompanying disclosure.

SUMMARY OF THE INVENTION

The present invention resides in perfluoroalkylene ether thioimidate esters having the following structural formula:

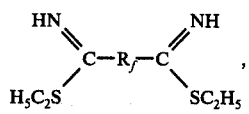

wherein $R_f$ is

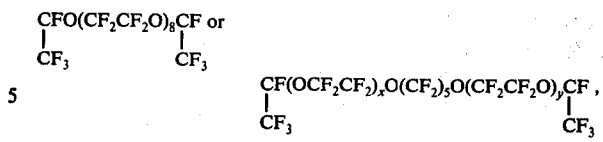

where $(x+y)$ equals 5 or 6.

In one embodiment, the present invention lies in a process for synthesizing the above-described compounds. The reaction involved in the synthesis can be represented by the following formula:

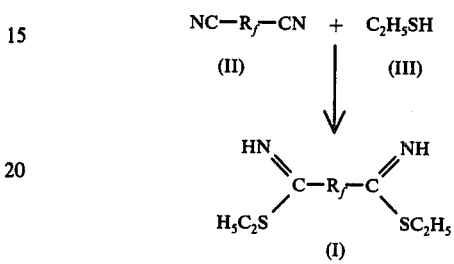

In the foregoing equation, $R_f$ is as indicated hereinabove.

The reaction represented by the foregoing equation is conducted by reacting an excess of ethanethiol (III) with the perfluoroalkylene ether dinitrile (II) in the presence of a catalytic amount of triethylamine. The amount of catalyst used can vary within rather broad limits, but it usually ranges from about 0.05 to 0.30 mole per mole of dinitrile. The mole ratio of ethanethiol to dinitrile is at least 2 to 1, e.g., 2 to 150:1. In addition to being a reactant, the ethanethiol functions as the reaction medium.

In conducting the process, it is usually preferred to add the dinitrile to a solution of triethylamine in ethanethiol. Upon completion of the addition, the resulting mixture is maintained at a temperature ranging from about room temperature to reflux temperature for a period of about 6 to 84 hours. In one procedure the mixture is allowed to remain at room temperature from about 24 to 72 hours after which it is refluxed for about 4 to 10 hours. At the end of the reaction period, the triethylamine and any excess ethanethiol are distilled off under atmospheric pressure and the thioimidate ester product is purified by vacuum distillation.

The perfluoroalkylene ether dinitriles used in preparing the diimidate esters of this invention can be prepared from perfluoroalkylene ether diacid fluorides by esterification, amidation and dehydration with phosphorus pentoxide as described hereinafter in Examples I-III. The procedure for preparing dinitriles is also described in U.S. Pat. No. 3,317,484 while U.S. Pat. Nos. 3,250,806, 3,250,807 and 3,960,814 disclose the preparation of diacid fluorides.

The thioimidate esters are particularly useful in preparing thermooxidatively and hydrolytically stable perfluoroalkylene ether bibenzoxazole polymers with improved low temperature viscoelastic properties. The polymers are prepared by the polycondensation of a thioimidate ester of this invention with a fluorocarbon ether bis(o-aminophenol) monomer. A more complete discussion of the synthesis of the polymers is contained in my copending application Ser. No. 817,658, filed on July 21, 1977, the disclosure of which is incorporated herein by reference. The outstanding combination of properties possessed by the polymers is attributed to the structure of the thioimidate ester monomers. Thus, the predominant portion of the perfluoroalkylene ether chain of the monomers is derived from tetrafluoroethylene oxide. As a result there is a substantial absence of pendant trifluoromethyl ($CF_3$) groups along the polymer chain, a condition that contributes to a high degree of chain flexibility and low polymer glass transition temperatures. However, the hexafluoropropylene oxide terminal units of the monomers do contain pendant $CF_3$ groups. When incorporated in the polymer chain, they become attached to the carbon atom at the 2-position of each benzoxazole ring. These $CF_3$ groups shield the benzoxazole rings from attack by water, thereby contributing toward the hydrolytic stability of the polymers.

A more complete understanding of the invention can be obtained by referring to the following illustrative examples which are not intended, however, to be unduly limitative of the invention.

EXAMPLE I

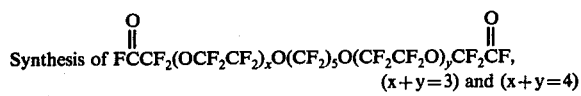

Synthesis of $FCCF_2(OCF_2CF_2)_xO(CF_2)_5O(CF_2CF_2O)_yCF_2CF$, (x+y=3) and (x+y=4)

Hexafluoroglutaryl fluoride (430 g, 1.73 mole) was added to a slurry of cesium fluoride (10 g) in tetraglyme (200 ml) and the mixture was stirred at 35°–40° C for one-half hour. The mixture was cooled to −5° C/−10° C and tetrafluoroethylene oxide was added through a vacuum manifold under a total pressure of 300–400 mm Hg. The reaction was monitored by frequent sampling and gas chromatographic analysis. It was terminated when 1880 g (9.2 moles) of tetrafluoroethylene oxide had been added. After warming to room temperature, the reaction product was separated from the solvent as the heavy phase (2,020 g). Gas chromatographic analysis of the crude product showed the following composition: $x+y=3$, 13.2%; $x+y=4$, 20.0%; $x+y=5$, 36.8% $x+y=6$, 14.2%; other 15.8% (mostly tetrafluoroethylene oxide homooligomers).

Distillation on a 15-plate Oldershaw column gave 151 g of $x+y=3$, b.p. 70°–79° C/1–2 mm and 200 g of $x+y=4$, b.p. 90°–93°/2 mm as well as 115 g of $x+y=5$, b.p. 109°–119° C/2–3 mm, and intermediate fractions.

Synthesis of 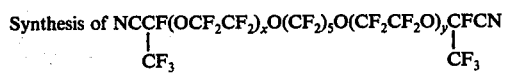

$FCOCF_2(OCF_2CF_2)_xO(CF_2)_5O(CF_2CF_2O)_yCF_2OCF$ (x+y=4) (200 g, 0.21 mole) was added to a slurry of cesium fluoride (2.5 g) in tetraglyme (50 ml) and the mixture was stirred for 30 minutes.

The mixture was cooled at −5°/−10° C and hexafluoropropylene oxide was added through a vacuum manifold at 400–500 mm Hg total pressure. The reaction was monitored by frequent sampling and gas chromatographic analysis. It was terminated when 95 g (0.57 mole) of hexafluoropropylene oxide had been added.

The fluorocarbon layer was separated from the solvent and was shown by gas chromatographic and nuclear magnetic resonance analysis to contain approximately 61% of the desired diacid fluoride,

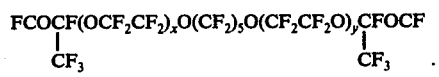

The above crude diacid fluoride was added to an excess of methanol and the mixture was stirred until the exothermic reaction had subsided. The reaction mixture was washed with water and dried over magnesium sulfate. The resultant diester, dissolved in Freon 113, was stirred in a 1-liter flask equipped with a dry ice-acetone condenser and a gas inlet tube. Anhydrous ammonia was added until it was heavily refluxing in the condenser. After stirring for several hours, the excess ammonia was allowed to escape and the solvent was removed under vacuum leaving in the flask 227 g of solid crude diamide.

The crude diamide was mixed with 300 g of $P_2O_5$ and the mixture was heated at 220°–240° C for several hours. The product volatiles were then distilled off under vacuum to give 211 g of crude product. Subsequent distillation gave 86 g of the desired product, b.p. 115°–118° C/1.0 mm. The product structure was verified by infrared and nuclear magnetic resonance spectral analysis which also indicated a small impurity in the form of the structural isomer,

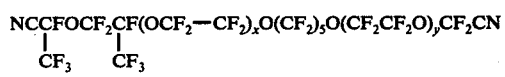

(x+y=5).

EXAMPLE II

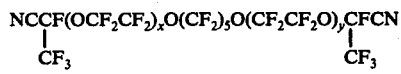

(x+y=5), b.p. 80°–81° C/12 mm, was obtained from

(x+y=3), using the same procedure as described in Example I. It also contained a small amount of the structural isomer,

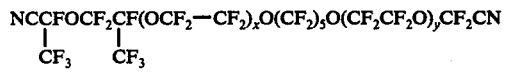

(x+y=4).

EXAMPLE III

Synthesis of $FCOCF_2OCF_2CF_2OCF_2COF$ $CF_2ICF_2OCF_2CF_2OCF_2CF_2I$ (55 g, 0.09 mole) and $ZnSO_4$ (0.6 g) were added to a three-neck flask equipped with a thermometer, reflux condenser, magnetic stirrer, dropping funnel and a gas inlet tube. The mixture was heated at 90° C and fuming sulfuric acid (200 g, 65% $SO_3$) was added while a slow flow of chlorine was bubbled through the solution. The temperature of the reaction mixture dropped to 70° C during the addition of sulfuric acid. After the addition was completed (30 minutes), the mixture was heated at 70° C and the addition of chlorine was continued for an additional 45 minutes (total chlorine: 3 g; 0.04 mole). After cooling to ambient temperature, the product, which separated as a clear colorless layer on top of the green-colored sulfuric acid layer, was decanted. Distillation gave 15 g (66.6% yield) of the product boiling at 80°–82° C. The product's structure was verified by infrared and nuclear magnetic resonance spectral analysis.

Synthesis of $\text{FCCF}_2(\text{OCF}_2\text{CF}_2)_6\text{OCF}_2\text{CF}$ (with two C=O groups)

$\text{FCOCF}_2\text{O}(\text{CF}_2)_2\text{OCF}_2\text{COF}$ (70 g, 0.2 mole) was added to a slurry of cesium fluoride (1 g) in tetraglyme (100 ml). The mixture was cooled at $-5°$ C to $0°$ C and tetrafluoroethylene oxide was added through a vacuum manifold. The reaction was monitored by frequent sampling for gas chromatographic analysis and it was terminated when 210 g (1.8 moles) of tetrafluoroethylene oxide had been added.

The fluorocarbon layer (141 g) was separated from the glyme layer and was distilled to give 30 g of the desired product, bp 65–67° C/0.1 mm Hg. The structure was verified by infrared and nuclear magnetic resonance spectral analysis.

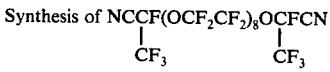
Synthesis of $\text{NCCF(OCF}_2\text{CF}_2)_8\text{OCFCN}$ with $\text{CF}_3$ groups $\text{FCOCF}_2(\text{OCF}_2\text{CF}_2)_6\text{OCF}_2\text{OCF}$ (48 g; 0.053 mole) was added to a slurry of cesium fluoride (1 g) in tetraglyme (35 ml). The mixture was cooled at $-8°$ C to $0°$ C and hexafluoropropylene oxide was added through a vacuum manifold. The reaction was monitored by frequent sampling and gas chromatographic analysis. The reaction was terminated when 42 g (0.25 mole) of hexafluoropropylene oxide had been added. The fluorocarbon layer was separated from the tetraglyme layer and was found to contain about 70% of the desired diacid fluoride.

The resultant mixture of diacid fluorides was esterified with methanol and the ester precipitated with water to give 82 g of crude dimethyl ester. The dry diester product was dissolved in 500 ml of Freon-113 solvent (trichlorotrifluoroethane) and gaseous dry ammonia was bubbled through the solution. Removal of the solvent under vacuum left 82 g of the crude diamide as a white waxy solid.

This crude diamide was mixed with 200 g of $P_2O_5$ and the mixture heated at 200°–240° C/100–150 mm Hg at which point it was refluxing gently. The nitrile product was distilled off under high vacuum to give 67 g of the crude dinitrile. Distillation on a spinning band column gave 32 g of the desired dinitrile 106–110/1.0 mm.

Gas chromatographic analysis and nuclear magnetic resonance spectral analysis indicated the presence of a small amount of impurity which was shown to be the structural isomer,

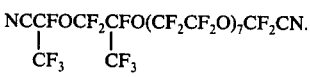
$\text{NCCFOCF}_2\text{CFO(CF}_2\text{CF}_2\text{O})_7\text{CF}_2\text{CN}$ with $\text{CF}_3$ groups.

EXAMPLE IV

A run was conducted in which a thioimidate ester of this invention was prepared in accordance with the reaction represented by the following equation:

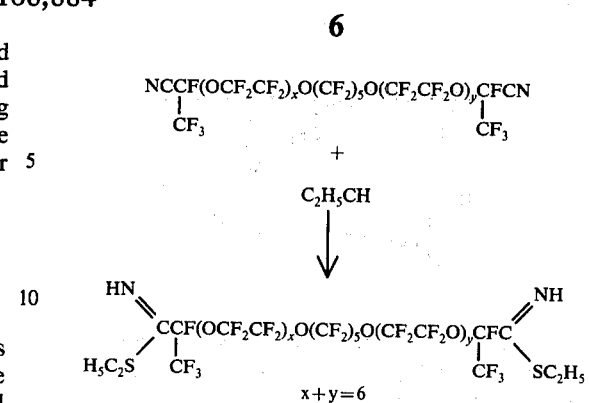

The perfluoroalkylene ether dinitrile as prepared in Example I (62.0 g, 0.005 mole) was added dropwise to a vigorously stirred solution of 3 ml of dry triethylamine in 50 ml of ethanethiol. The resultant two-phase solution was stirred at room temperature for 72 hours and then at reflux for 8 hours. The excess ethanethiol and triethylamine were distilled from the clear one-phase solution at atmospheric pressure. Distillation of the yellow oily residue yielded 55.7 g (82% yield) of water white product, bp 164°–167° C/0.05 mm.

Analysis Calc'd: C,23.94; H,0.89; N,2.07; S,4.73.
Found: C,23.93; H,0.68; N,2.20; S,4.59.
Molecular Weight (mass spectroscopy): Calc'd: 1354.
Found: 1354.

EXAMPLE V

A run was conducted in which a thioimidate ester of this invention was prepared in accordance with the reaction represented by the following equation:

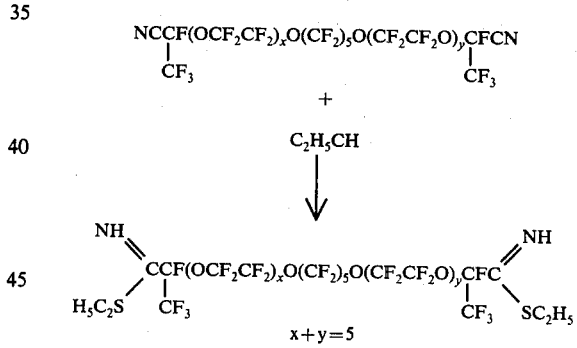

To a vigorously stirred solution of 1 ml of dry triethylamine in 20 ml of ethanethiol was added dropwise the perfluoroalkylene ether dinitrile (20.7 g, 0.017 mole) as prepared in Example II. The temperature of the reaction mixture was maintained at room temperature both during the addition and for an additional 72 hours. Then the reaction mixture was refluxed for 6 hours and the excess triethylamine and ethanethiol were distilled over at atmospheric pressure. Distillation of the clear, pale yellow residue yielded 12.7 g (61% yield) of water white product, bp 152°–153° C/0.05 mm.

Analysis Calc'd: C,24.25; H,0.98; N,2.26; S,5.18.
Found: C,24.46; H,0.98; N,2.76; S,5.13.
Molecular weight (mass spectroscopy): Calc'd: 1238.
Found: 1238.

EXAMPLE VI

A run was conducted in which a thioimidate ester of this invention was prepared in accordance with the reaction represented by the following equation:

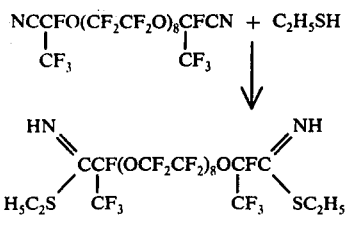

The perfluoroalkylene ether dinitrile as prepared in Example III (20.4 g, 0.017 mole) was added over a five-minute period to a vigorously stirred solution of 1 ml of dry triethylamine in 20 ml of ethanethiol. The temperature of the resultant two-phase reaction mixture was maintained at 35° C for 24 hours at which time the triethylamine and excess ethanethiol were distilled off. The resultant dark yellow residue was then distilled to yield 17 g (81% yield) of water white product, bp 146°–149° C/0.03 mm.

Analysis Calc'd: C,23.65; H,0.92; N,2.12; S,4.85.
Found: C,23.75; H,0.65; N,2.01; S,4.71.
Molecular weight (mass spectroscopy): Calc'd: 1320. Found: 1320.

As seen from the foregoing, the thioimidate esters of this invention are derived primarily from tetrafluoroethylene oxide and are end-capped with hexafluoropropylene oxide. The substantial absence of $CF_3$ groups in the perfluoroalkylene ether chain and the presence of $CF_3$ groups in the terminal portions of the chain makes it possible to use the compounds to synthesize thermooxidatively and hydrolytically stable perfluoroalkylene ether bibenzoxazole polymers with improved low temperature viscoelastic properties.

As will be evident to those skilled in the art, modifications of the present invention coming within the spirit and scope of the invention can be made in view of the foregoing disclosure.

I claim:

1. A thioimidate ester having the following formula:

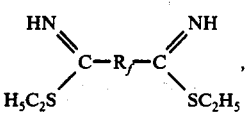

wherein $R_f$ is

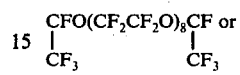

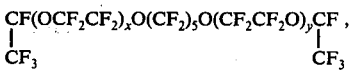

where $(x+y)$ equals 5 or 6.

2. The thioimidate ester according to claim 1 in which $R_f$ is

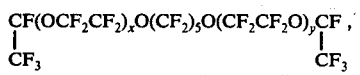

where $(x+y)$ equals 5 or 6.

3. The thioimidate ester according to claim 2 in which $(x+y)$ equals 5.

4. The thioimidate ester according to claim 2 in which $(x+y)$ equals 6.

5. The thioimidate ester according to claim 1 in which $R_f$ is

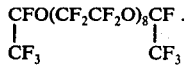

* * * * *

UNITED STATES PATENT AND TRADEMARK OFFICE
CERTIFICATE OF CORRECTION

PATENT NO. : 4,108,884

DATED : August 22, 1978

INVENTOR(S) : Robert C. Evers

It is certified that error appears in the above-identified patent and that said Letters Patent are hereby corrected as shown below:

Column 6, lines 6 and 40, "$C_2H_5CH$," each occurrence, should read -- $C_2H_5SH$ --.

Signed and Sealed this

First Day of May 1979

[SEAL]

Attest:

RUTH C. MASON
*Attesting Officer*

DONALD W. BANNER
*Commissioner of Patents and Trademarks*